US005800785A

United States Patent [19]

Bochner

[11] Patent Number: 5,800,785
[45] Date of Patent: Sep. 1, 1998

[54] TESTING DEVICE FOR LIQUID AND LIQUID SUSPENDED SAMPLES

[75] Inventor: Barry Bochner, Alameda, Calif.

[73] Assignee: Biolog, Inc., Hayward, Calif.

[21] Appl. No.: 685,695

[22] Filed: Jul. 24, 1996

Related U.S. Application Data

[63] Continuation of Ser. No. 584,989, Jan. 8, 1996, Pat. No. 5,589,350, which is a continuation of Ser. No. 462,443, Jun. 5, 1995, abandoned, which is a continuation of Ser. No. 972,625, Nov. 6, 1992, abandoned.

[51] Int. Cl.$^6$ .................................................. B01L 11/00
[52] U.S. Cl. .......................... 422/101; 422/99; 422/102; 435/29; 435/287.7; 435/288.5; 435/300.1; 435/301.1
[58] Field of Search ........................ 422/99–104; 435/29, 435/287.7, 288.5, 300.1, 301.1

[56] References Cited

U.S. PATENT DOCUMENTS

| | | | |
|---|---|---|---|
| 3,953,566 | 4/1976 | Gore | 264/288 |
| 3,963,355 | 6/1976 | Aldridge, Jr. et al. | 356/201 |
| 4,038,151 | 7/1977 | Fadler et al. | 195/127 |
| 4,129,483 | 12/1978 | Bochner | 195/100 |
| 4,187,390 | 2/1980 | Gore | 174/102 |
| 4,235,964 | 11/1980 | Bochner | 435/34 |
| 4,777,021 | 10/1988 | Wertz et al. | 422/101 |
| 4,806,316 | 2/1989 | Johnson et al. | 422/100 |
| 4,948,442 | 8/1990 | Manns | 156/73.1 |
| 4,952,373 | 8/1990 | Sugarman et al. | 422/99 |
| 5,039,493 | 8/1991 | Oprandy | 422/101 |
| 5,047,215 | 9/1991 | Manns | 422/101 |
| 5,100,626 | 3/1992 | Levin | 422/100 |
| 5,110,555 | 5/1992 | Moore et al. | 422/100 |
| 5,134,063 | 7/1992 | Bochner | 435/29 |
| 5,141,868 | 8/1992 | Shanks et al. | 435/288 |
| 5,342,581 | 8/1994 | Sanadi | 422/101 |
| 5,462,874 | 10/1995 | Wolf et al. | 435/297.5 |
| 5,601,991 | 2/1997 | Oberhardt | 435/7.91 |

OTHER PUBLICATIONS

B.R. Bochner, Nature 339:157 (1989).
B.R. Bochner, ASM News 55:536 (1990).
B.R. Bochner, Am. Clin. Lab., Apr.:14 (1991).
B. Bochner and M. Savageau, Appl. Environ. Microbiol., 33:434 (1977).
C.D. Marotta, MD&DI, Dec.:24 (1986).
J.L. Brash, Annals N.Y. Acad. Sci., 283:356 (1977).
Gelman Sciences, News for Immediate Release (undated) describing Repel™ and Versapel™.
Vitek Product Literature for Test Cards.
Viteck, Food and Drug Packaging, Dec., 1989.
Polyfiltronics, Innovation in Diagnostic and Medical Devices, Summer 1991.
Chromex Corp. Product Brochure for Interflo®.
Porex, Solution News, Winter 1987.

*Primary Examiner*—Harold Y. Pyon
*Attorney, Agent, or Firm*—Medlen & Carroll, LLP

[57] ABSTRACT

Testing of samples in a small, closed, and easy-to-fill device. Simultaneous filling of a large number of test wells using a novel gas-venting design, allowing for multiparameter testing and/or identification of bacteria.

21 Claims, 6 Drawing Sheets

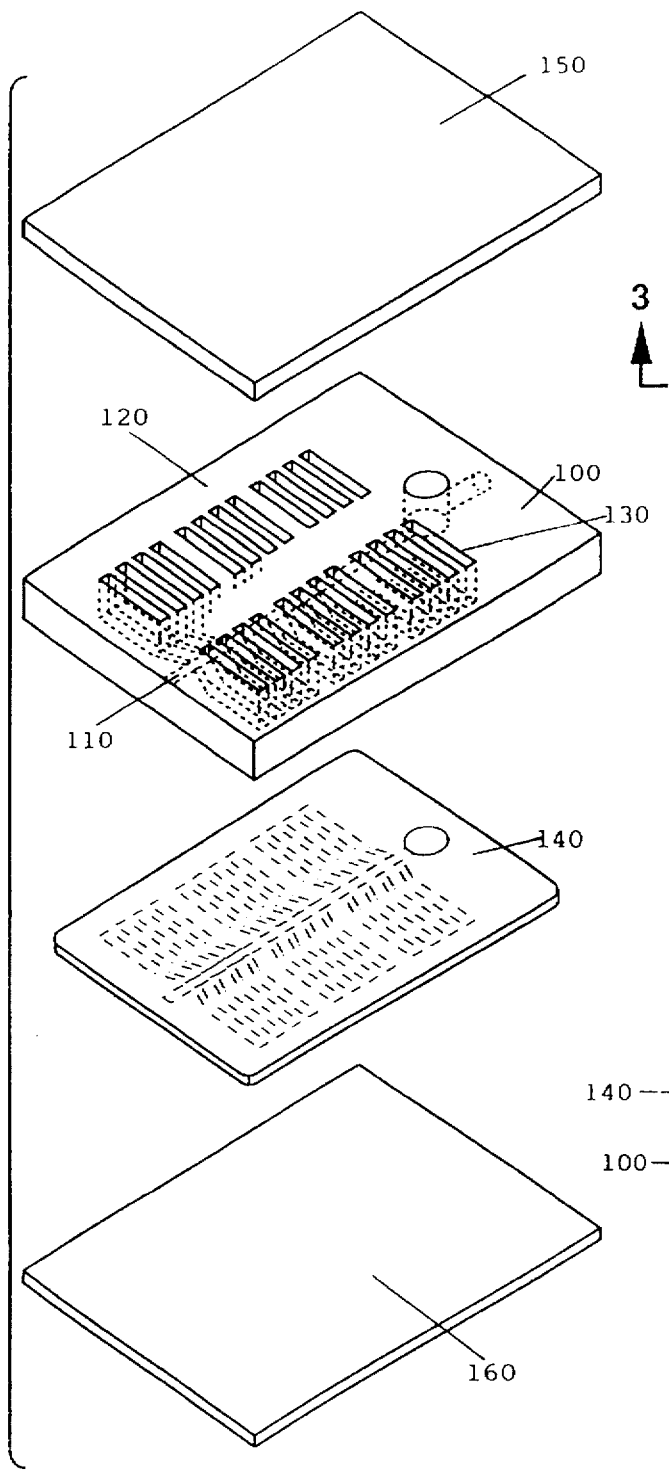
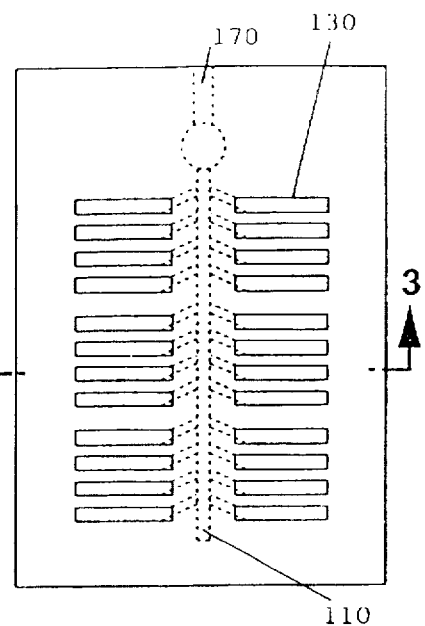
FIG. 2
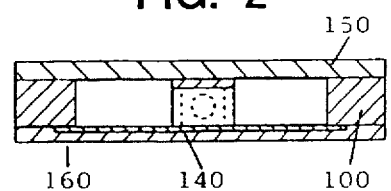
FIG. 3
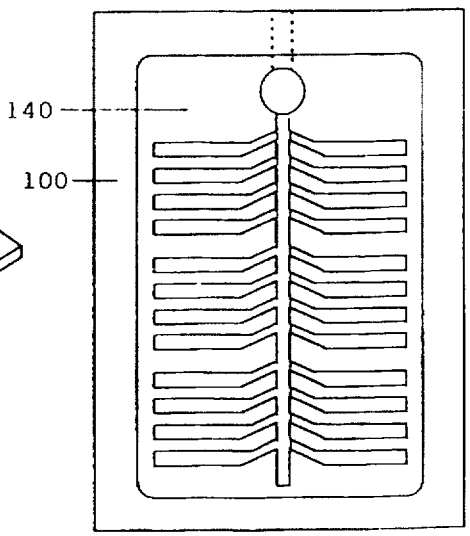
FIG. 1      FIG. 4

TESTING DEVICE FOR LIQUID AND LIQUID SUSPENDED SAMPLES

This application is a Continuation of U.S. application Ser. No. 08/584,989, filed Jan. 8, 1996, now U.S. Pat. No. 5,589,350, which is a Continuation of U.S. application Ser. No. 08/462,443, filed Jun. 5, 1995, now abandoned, which is a Continuation of U.S. application Ser. No. 07/972,625, filed Nov. 6, 1992, now abandoned.

FIELD OF THE INVENTION

The invention generally relates to a small, closed, easy-to-use device for performing chemical, biochemical, immunological, biomedical, or microbiological tests, and in particular to a device for the multiparameter testing and/or identification of bacteria.

BACKGROUND

Modern diagnostic medicine depends on the routine testing of biological samples from sources such as blood, serum, spinal fluid, urine, tissue specimens, etc. In addition, many other industries and research facilities run both chemical and biological tests in large numbers. In order to perform the running of large numbers of tests efficiently, accurately, and safely, the "hardware" used in the performance of the tests can be of critical importance.

Microtiter plates or "microplates" were introduced in the 1960's to facilitate laboratory testing in situations where a large number of tests were run simultaneously. The most typical microplates contain ninety-six (96) molded plastic wells (in an 8×12 array) with a typical sample volume capacity of about 200 microliters. A wide variety of mechanical fluid handling devices are now available so that specimens, chemical solutions and other liquids can be transferred into the wells. Usually a row of eight (8) or twelve (12) wells are filled simultaneously, but some handling devices can simultaneously add sample to all of the wells.

The design of the microplate is less than optimal in several ways. First, the microplate wells are open wells. Most microplates have loose fitting lids, but these do not seal the top of the well. As a consequence, liquid can spill out of the well or aerosols can form during filling. This can ruin the test and may also create a hazard if the testing involves infectious material. Moreover, liquid can evaporate from the wells. This can also ruin the test or limit the duration of the test. Thus, it is preferable to have testing hardware which can be easily sealed.

Second, although filling devices are available to fill more than one well at a time, these devices are costly and still time consuming to use. It would, therefore, be preferable for the testing device to be easy and fast to fill without expensive equipment.

Third, the volume of the well is relatively large. Often the sample is in short supply or the testing reagents are costly. It would, therefore, be preferable to have wells with a smaller capacity.

Finally, microplates are relatively large and heavy. They take up a great deal of space in the laboratory refrigerators and incubators, and they are costly to ship in large quantities.

An improvement over the microplate format is disclosed in U.S. Pat. No. 4,038,151 to Fadler et al. This device has an enclosed format (minimizing spills and aerosols) and is relatively smaller and lighter in weight. The well volume is reduced and thus requires a smaller sample size.

Nonetheless, this design has distinct disadvantages as well. In order to fill the Fadler test device with liquid, the air in the wells must leave so that the liquid can enter. The Fadler et al. device accomplishes this with a very slow, elaborate, and expensive procedure in which the device is placed in a vacuum chamber and the air is removed as the vacuum is created. When the vacuum is released, the liquid flows into the device. Since, even with the elaborate vacuum system, the air removal may not be complete, this design provides a small well connected to each main well as an appendage for the purpose of holding residual air. These appendage wells, take up space that might otherwise be used to accommodate more test wells.

An alternative to this design is disclosed in U.S. Pat. No. 4,806,316 to Johnson et al. This device allows air to escape from the wells via escape channels which connect back to the air space in the reservoir from which the sample originates. This additional channelling is necessary so that the liquid can flow to the wells. Not only does this additional channelling take up space in the device making it larger or reducing the number of test wells that will fit on it, but, more importantly, this design requires the use of a reservoir with a special cap having two vent pipes, which is an expensive component when, for reasons of potential contamination, such reservoir and cap must be single-use and disposable.

What is needed is a device that is simpler, faster and more economical to fill. Such a device should not require the use of filling procedures having additional risk nor which require expensive and cumbersome equipment, but it should be able to accommodate the simultaneous filling of a large number of test wells.

SUMMARY OF THE INVENTION

The invention generally relates to the chemical, biochemical, immunological, biomedical, or microbiological testing of a sample in a small, closed and easy-to-fill device, and in particular to the multiparameter testing of microorganisms for the purpose of identification or for other purposes. Depending on the type of test being run, such device might contain one or more dry test chemicals, or it may, initially, be empty. The device requires only a small volume of sample (e.g., one milliliter).

The invention represents a much improved and fundamentally different design. The invention contemplates permitting air in the device to escape during filling by taking advantage of the physical properties of some newly available materials that act as vents. These materials have the useful property that they allow gas to pass readily, and yet they provide a strong barrier to aqueous liquids. In this manner, discrimination is made between liquids and gasses without the need for a valve-like mechanism.

The barrier to the passage of liquids can be achieved in several ways. One way is for the liquid-contacting surfaces of the material, particularly internally within its pores, to be hydrophobic so as to repel the liquid and thereby making it difficult for the liquid to pass through the material. Another way for the material to prevent the passage of gas would be for it to swell and close off the pores when contacted by liquid; and yet still another way would be for it to form a film or gel which would effectively plug or close the pores upon exposure to liquid. By incorporating one of such venting materials into the design, a simple means is provided for permitting air to escape from the testing device during filling, while preventing the escape of liquid. Such a fluid flow discriminator operates automatically, without any moving parts.

In one embodiment, the present invention contemplates a device comprising: a) a housing; b) a testing region contained within said housing; c) a liquid receiving means on an external surface of said housing; d) a liquid flow-directing means providing liquid communication between said testing region and said liquid receiving means; and e) a gas-venting, liquid barrier in fluidic communication with said testing region.

It is contemplated that a test sample, such as a suspension of microorganisms in water or saline solution, would be taken up in liquid form by a pipette or other suitable means and delivered, under positive pressure, to the wells within the housing by way of the port and the connecting channels. It is further contemplated that as the liquid fills the connecting channels, the air within the device would exit through the gas-venting, liquid barrier ahead of the advancing liquid.

After venting is complete, a non-venting material may be affixed to cover the exposed outside surface of the barrier thereby sealing it against the evaporation of the liquid through the vent material. Such non-venting material can be one of any number of tapes each differing in its ability to permit the molecular diffusion of oxygen so as to allow the desired amount of oxygen to enter or leave the well as may be needed for maintaining the appropriate environment for the microorganisms or test chemistry within.

Following the filling, a non-venting tape can also be applied to cover over the filling port. In this manner, the present invention provides a device wherein the microorganisms are completely contained so that little hazard exists of having spills or aerosols and the device is convenient and easy to handle. In a preferred embodiment, the non-venting tape is a plastic film, e.g., Mylar.

It is not intended that the present invention be limited to particular materials. In one embodiment, the housing is made of hard plastic such a polystyrene. In a preferred embodiment, the gas-venting, liquid barrier is a membrane or plug made of a porous, hydrophobic material that is capable of allowing air to pass readily during delivery of the liquid under positive pressure, yet which will block the flow of liquid under the positive pressure normally applied in the practice of the invention.

In one embodiment, the gas-venting, liquid barrier is made of material selected from the group comprising polycarbonate, polypropylene, and polysulfone. In another embodiment, the gas-venting, liquid barrier is made of material selected from the group comprising polyvanilidine chloride (PVDC) and polyvanilidine difluoride (PVDF). In still another embodiment, the gas-venting, liquid barrier is made of expanded, sintered polytetrafluoroethylene (PTFE).

As a membrane, the pore size for these materials is generally greater than or equal to 0.1 microns, and preferably greater than 3.0 microns. The positive pressure normally applied in the practice of the invention will be greater than 1 pound per square inch (psi), and preferably greater than 5 psi. The gas-venting, liquid barrier in one embodiment blocks the passage of liquid at pressures less than 75 pounds per square inch.

It is also not intended that the invention be limited to any particular configuration of wells within the housing, or to any one configuration of channels within the housing.

In one embodiment, the channels in communication with the wells are of decreasing cross-section.

It is also not intended that the invention be limited to the type of sample. The present invention can be employed with success with all types of liquid samples, including suspensions of biological material. It is also not intended that the invention be limited by the type of suspended microorganism. The device of the present invention is useful for identification of a great number of microorganism species and subspecies.

In a preferred embodiment, the device can be held conveniently in a user's hand. Due to its small size, the device conserves media and test chemicals. It is also preferred that the background color of the device be uniform (e.g., white polystyrene or clear polystyrene). In this manner, the results of the test can be read as a visual change either by eye or, alternatively, by a simple or automated instrument. In the case of an opaque background the test would be read by reflected light, and in the case of a transparent background the test could be read by transmitted light. In any case, one of each well's surfaces must be transparent to permit it to be read.

While the actual placement of the barrier may have an impact on the nature of the background (i.e., opaque or transparent), it is not intended that the barrier be positioned in only one manner. The invention contemplates an embodiment wherein the barrier is adapted to completely enclose one of the sides of the testing wells. However, the invention contemplates an embodiment wherein the barrier is adapted to be only a portion of one of the sides of the well. In still another embodiment, it is contemplated that the barrier is internal to the wells. In yet another embodiment, it is contemplated that the barrier is separated from the well by a conduit. The conduit itself can be configured in a number of ways (e.g., tube, passageway, etc.).

The present invention also contemplates a method for testing chemical or biological samples. In one embodiment, the invention comprises: (a) providing a sample in liquid form; (b) providing a sample delivering means; (c) providing a device comprising: i) a housing, ii) a testing region contained within said housing, iii) a liquid receiving means on an external surface of said housing, iv) a liquid flow-directing means providing liquid communication between said testing region and said liquid receiving means, and v) a gas-venting, liquid barrier in fluidic communication with said testing region; and (d) delivering, internal to said housing, said sample via said sample delivering means to said testing region such that said liquid enters said device at said liquid receiving means under positive pressure and the air in said device is vented through said gas-venting liquid barrier.

In one embodiment, the method further comprises, prior to step (d), prefilling said test wells with a test formula. For example, the test formula may comprise basal medium, one or more carbon sources, and an indicator, such as a redox indicator.

The device can be configured such that the sample can be delivered without the need for cumbersome equipment. In such an embodiment, the liquid receiving means may comprise one or more liquid entry ports on an external surface of said housing and the sample delivering means may comprise a pipette adapted to fit the liquid entry port. For better fit, the port can be configured with internal grooves and the pipette can be molded with corresponding threads (or the pipette can be molded with internal grooves and the port can be configured with corresponding threads) so that a substantially liquid-tight seal is formed.

DESCRIPTION OF THE FIGURES

FIG. 1 is an exploded perspective view of one embodiment of the device of the present invention.

FIG. 2 is a top plan view of the device shown in FIG. 1.

FIG. 3 is a cross-sectional view of the device shown in FIG. 2 along the lines of 3—3.

FIG. 4 is a bottom plan view of the device shown in FIG. 1.

DESCRIPTION OF THE INVENTION

Figures 5, 6, 7:
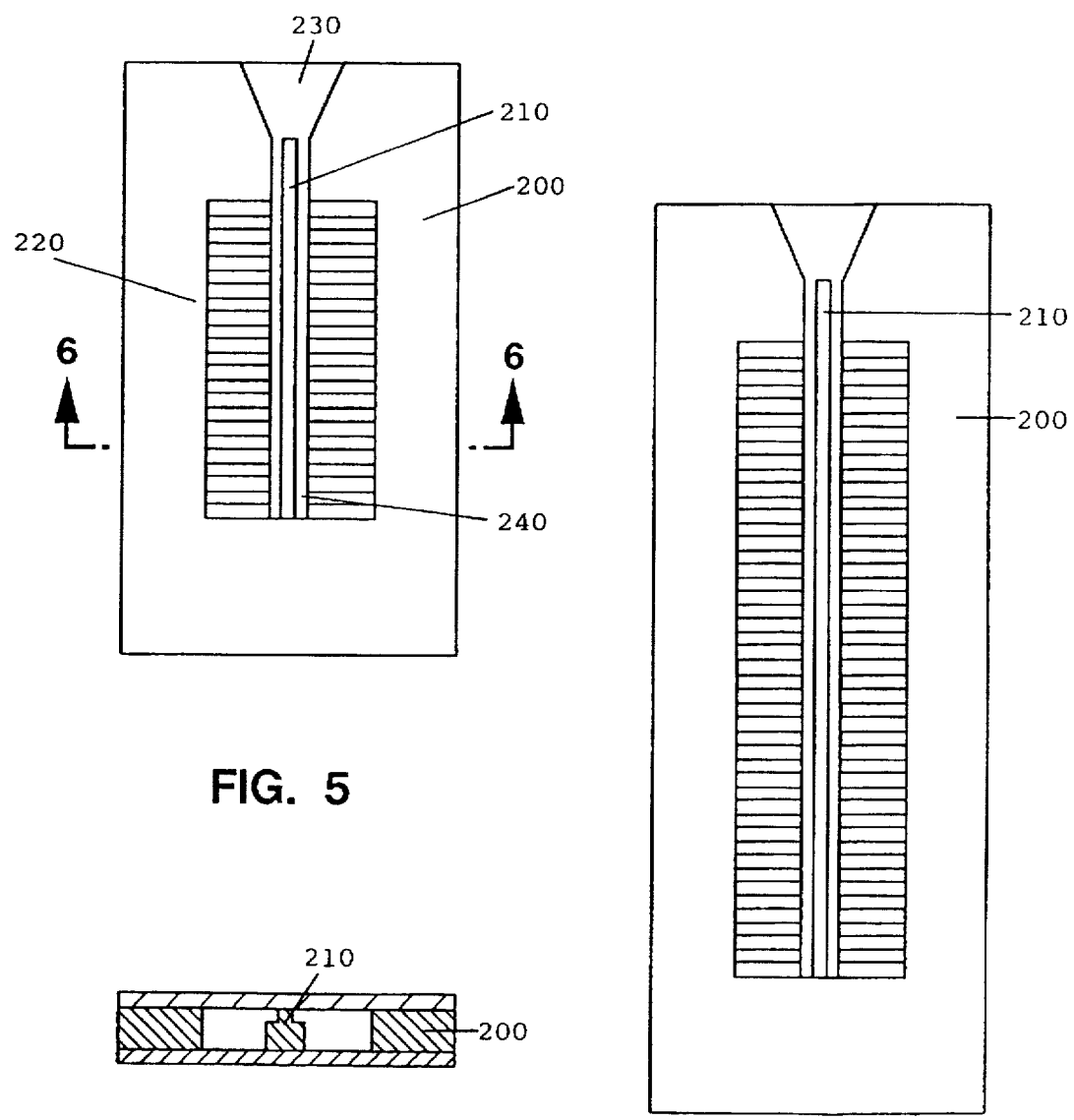
FIG. 5 is a top plan view of a second embodiment of the device of the present invention.
FIG. 6 is a cross-sectional view of the device shown in FIG. 5 along the lines of 6—6.
FIG. 7 is a top plan view of a third embodiment of the device of the present invention.

The invention generally relates to a device for the single or multiparameter testing, of chemical, biochemical, immunological, biomedical, or microbiological samples in liquid or liquid suspension form in a small, closed, easy-to-fill device, and is particular suitable for multiparameter testing and identification of microorganisms. To this end, the present invention contemplates a device comprising: a) a housing; b) a testing region contained within said housing; c) a liquid receiving means on an external surface of said housing; d) a liquid flow-directing means providing liquid communication between said testing region and said liquid receiving means; and e) a gas-venting, liquid barrier in fluidic communication with said testing region.

After the device has been filled, a non-venting, sealing tape can be applied to the device to cover the gas-venting, liquid barrier to reduce the evaporation of the liquid from the device; the tape can permit the molecular diffusion of oxygen into or out of the device to maintain the desired chemical or biochemical environment within the device for successful performance of the test. Where the liquid receiving means comprises liquid entry ports, a similar closing tape can be applied to close the port or ports to prevent spilling and evaporation of the liquid therefrom.

One of the principal objects of the present invention is to provide, unlike other approaches, a method and device for carrying out chemical, biochemical, immunological and microbiological tests which greatly simplifies the removal of air to allow filling. A further object is to provide a closed, spill-proof device which is small and compact and easy to read either by eye or by automated instrumentation wherein the visible result of the test within the device can be detected spectrophotometrically by passing light through the sample, or the visible result can be detected by imaging such as with a video camera. The results, however read, can be inputted into a computer wherein an algorithm then determines the best match of the inputted pattern to the patterns of known species in a data base.

The small size and spill-proof configuration of the present device permits many such devices to be held in a cartridge, similar to those that hold 35 mm photographic slides for viewing in a Kodak™ Carousel slide projector or a Kodak™ slide-to-video converter. Such cartridge and reading mechanism can be housed within a temperature controlled enclosure wherein the devices can be incubated and read automatically. The visual result that is detected by eye or by instrument can be any optically perceptible change such as a change in turbidity, a change in color, or the emission of light, such as by chemiluminescence, bioluminescence, or by Stokes shift. Color indicators may be, but are not limited to, redox indicators (e.g., tetrazolium), pH indicators, or various dyes and the like. Various dyes are described in U.S. Pat. Nos. 4,129,483, 4,235,964 and 5,134,063 to Barry R. Bochner, hereby incorporated by reference. See also B. R. Bochner, Nature 339:157 (1989); Bochner, B. R. ASM News 55:536 (1990); B. R. Bochner, Amer. Clin. Lab. April: 14 (1991). A generalized indicator useful for practice of the present invention is also described by Bochner and Savageau. See B. Bochner and M. Savageau, Appl. Environ. Microbiol. 33:434 (1977).

Testing based on the redox technology is extremely easy and convenient to perform. A cell suspension is prepared and introduced into the testing wells of the device. Each well is prefilled with a different substrate.

In a preferred embodiment, all wells are prefilled with test formula comprising a basal medium that provides nutrients for the microorganisms, and a color-change indicator, and each well is prefilled with a different carbon compound or "substrate," against which the microorganism is tested. "Basal medium," as used herein, refers to a medium which provides nutrients for the microorganisms, but does not contain sufficient concentrations of carbon compounds to trigger a color response from the indicator. "Carbon compound," "carbon source" and "substrate" are equivalent terms, and are used interchangeably herein to refer to a carbon chemical in sufficient concentration as to trigger a color response from the indicator when it is utilized (metabolized) by a microorganism.

One of the principal uses of the present invention is as a method and device for simple testing and speciation of microorganisms. The present invention contemplates microbiological testing based on the redox technology discussed above wherein microorganism cells are removed from a culture medium on which they have been grown and are suspended in saline or water at a desired density. This suspension is then introduced into the wells of the testing device which have been prefilled with basal medium, indicator, and substrate chemicals. The method is extremely easy and convenient to perform, and, unlike other approaches, the method and device do not require skilled personnel and cumbersome equipment.

DESCRIPTION OF THE PREFERRED EMBODIMENTS

As shown in FIGS. 1-4, an embodiment of the device of the present invention comprises a housing (100) containing a channel (110) providing communication to a testing region (120) so that a liquid (not shown) can flow into a plurality of wells (130). The channel (110) is enclosed by the surface of a hydrophobic, gas-venting membrane (140) adapted for forming one surface of the wells (130) and attached to one side of the housing (100). The housing (100) can be sealed on its other side by a solid base (150). In other embodiments, a flexible tape (not shown) could be substituted for the solid base (150) or the solid base (150) could be molded so as to be integral with the housing (100).

After filling the device with the liquid (not shown) an optional non-venting material such as tape (160) can be adhered to the outer surface of the gas-venting membrane (140) to seal it against evaporation of the liquid within the device through the gas-venting membrane.

In use, the liquid sample (not shown) can be added via an open-air, liquid entry port (170) using a sample delivering means (not shown) such that liquid enters the housing (100) under positive pressure and makes communication with each of the plurality of test wells (130), whereby the air within the device is displaced and vented through the hydrophobic, gas-venting membrane (140).

FIGS. 5–7 show an embodiment in which the housing (200) has a raised internal ridge (210) that serves to split the liquid stream (not shown). The testing region (220) is in communication with the open-air, liquid entry port (230) via a channel (240). The testing region (220) can be small (FIG. 5) or large (FIG. 7) to accommodate multiparameter testing.

Figure 8:
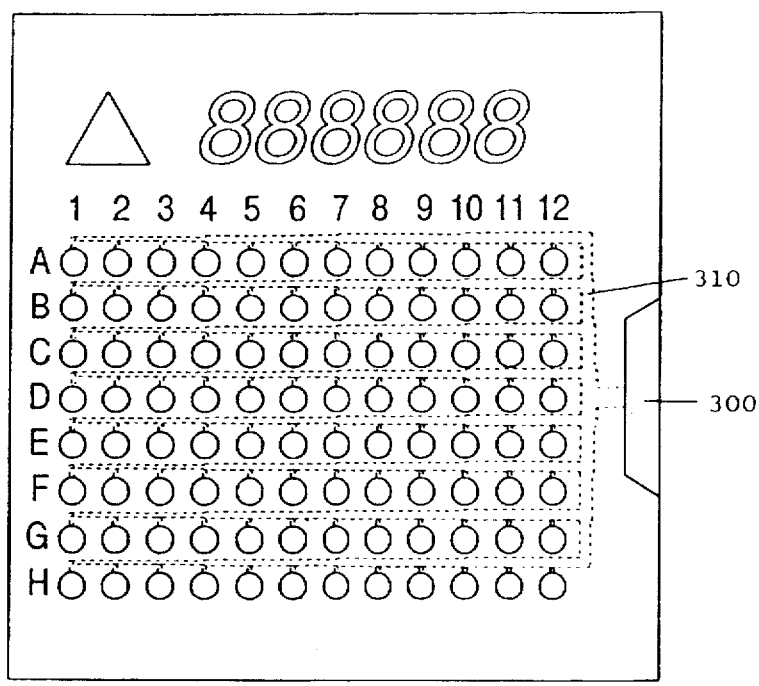
FIG. 8 is a top plan view of a fourth embodiment of the device of the present invention.
Figure 9:
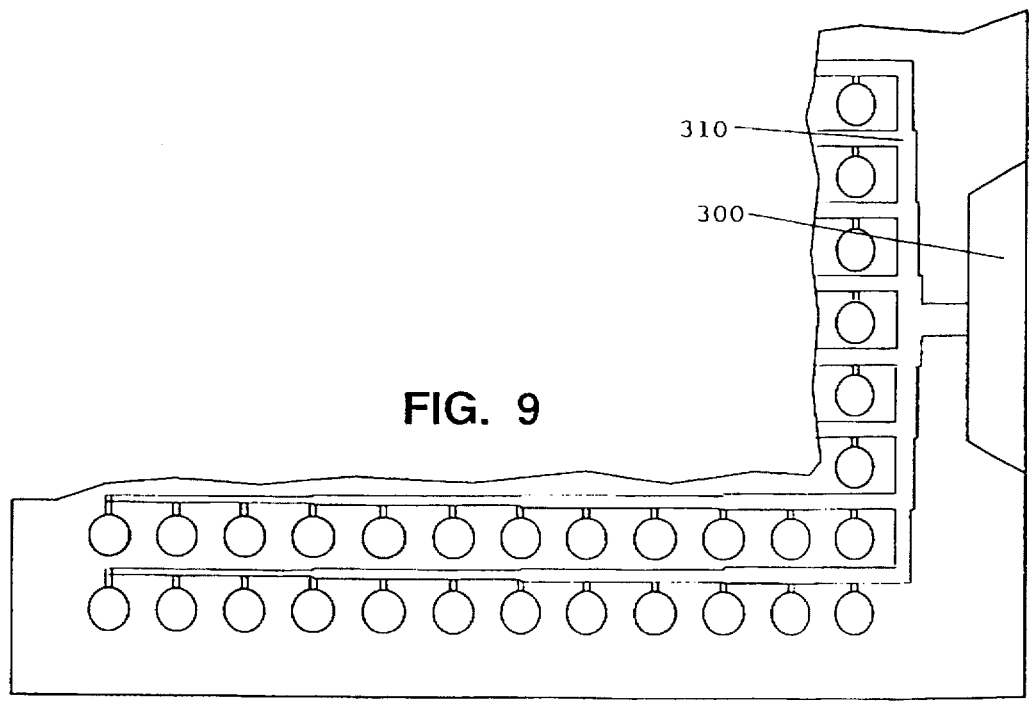
FIG. 9 is an enlarged bottom plan view of FIG. 8.
Figure 10:
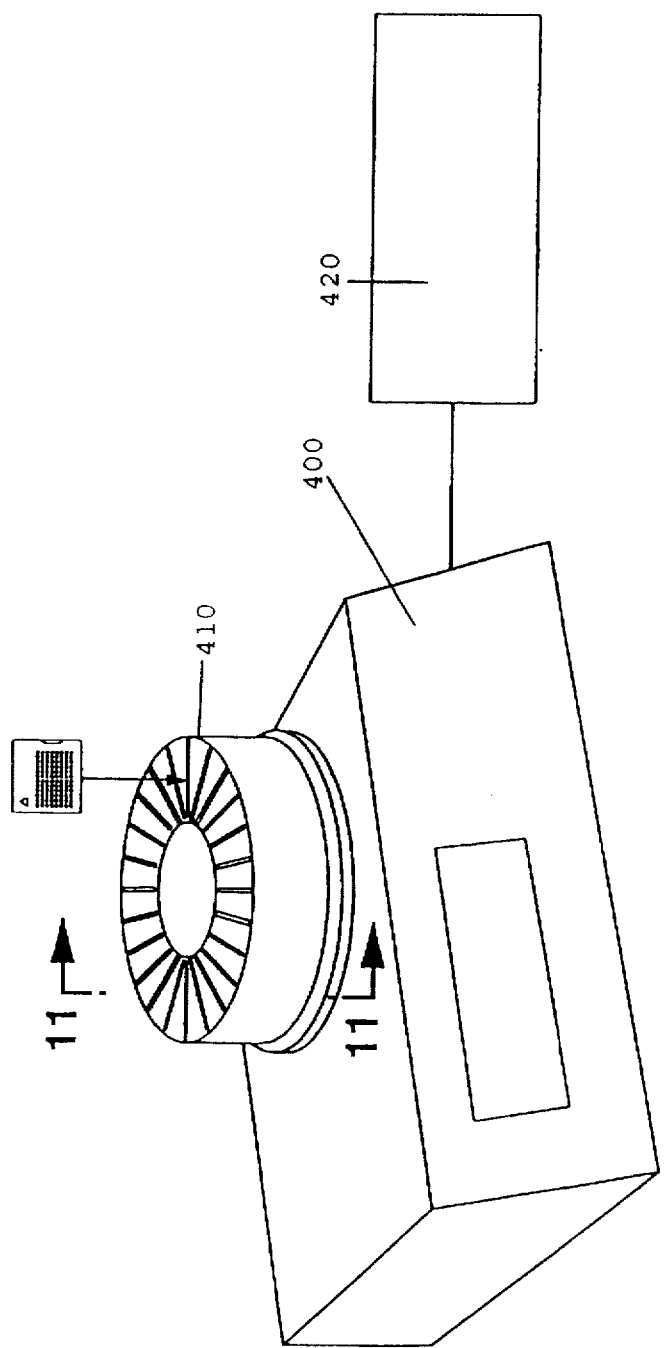
FIG. 10 is one embodiment of an automated analyzer for reading the embodiment of the device shown in FIGS. 8 and 9.
Figure 11:
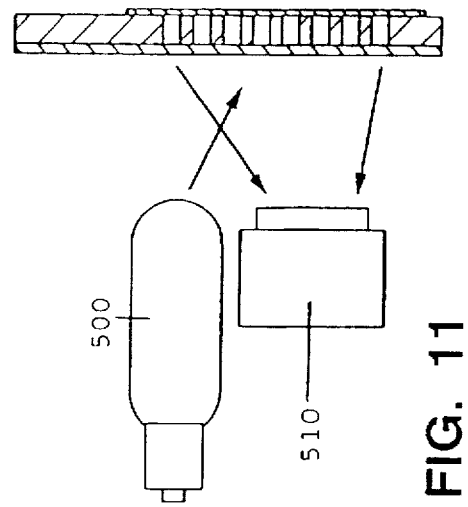
FIG. 11 is a cross-section of the analyzer of FIG. 10.

FIGS. 8 and 9 show a preferred embodiment of the device of the present invention wherein ninety six (96) testing wells are in communication with an entry port (300) via channels (310) of decreasing cross-section. This embodiment is adapted to fit into a cartridge (410) of an automatic analyzer (shown schematically in FIG. 10 as element 400) in the manner that a 35 mm photographic slide fits into a slide projector cartridge, and read to produce an output (shown schematically in FIG. 10 as element 420). The slide cartridge and/or the entire automatic analyzer can be enclosed in a temperature controlled and/or humidity controlled incubator housing (not shown) to establish the desired environment for the test. The analyzer may read the device in any number of ways including reflected light, transmitted light, or emitted light. However, in a preferred embodiment a light source (shown schematically in FIG. 11 as element 500) directs light at the surface of the device such that light reflected from color in the test wells can be detected by a video camera type pickup (shown schematically in FIG. 11 as element 510).

As mentioned above, it is not intended that the barrier be positioned in only one manner. While FIGS. 1–7 show embodiments wherein the barrier is adapted to completely enclose one of the sides of the testing wells, other positioning is contemplated.

Figure 12:
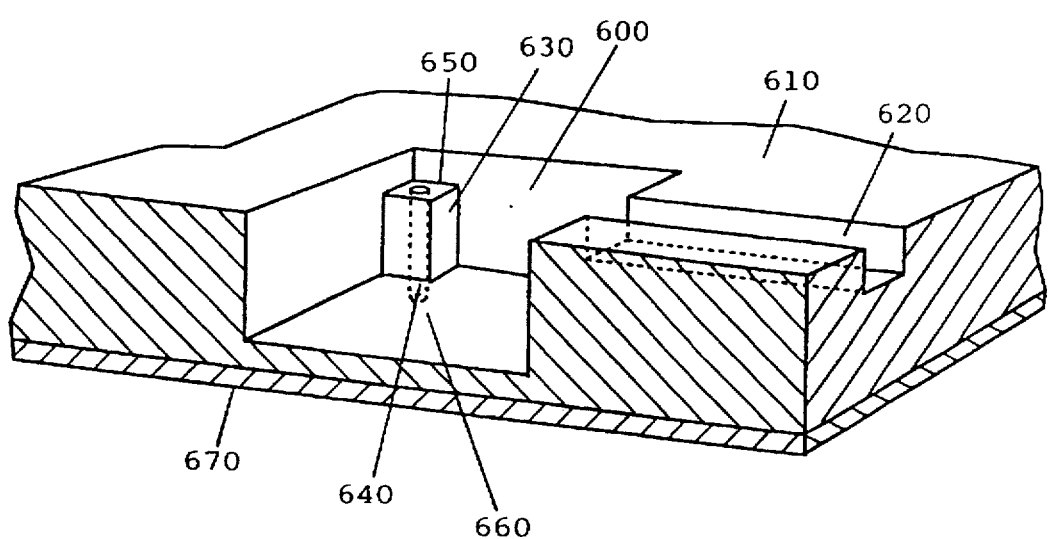
FIG. 12 is a perspective view of a fifth embodiment of the device of the present invention.

FIG. 12 shows a well (600) which could be part of larger testing region (not shown) on a housing (610) of the device of the present invention. A channel (620) is indicated for liquid communication with a liquid receiving means (not shown). In a corner of one side of the well (600) is a vent housing (630) having an internal conduit (640). The conduit has an internal surface (650) and an external surface (660) which connects to the barrier (670). In this embodiment, the barrier (670) is separated from the well (600) by the conduit (640).

In other embodiments, the barrier (not shown) can be configured as a plug to fit the shape of the conduit. Alternatively, the barrier (not shown) can take the form of a membrane and be placed on the internal surface (650) of the conduit (640). When on the internal surface (650) the barrier (not shown) is internal to the well (600).

Figure 13:
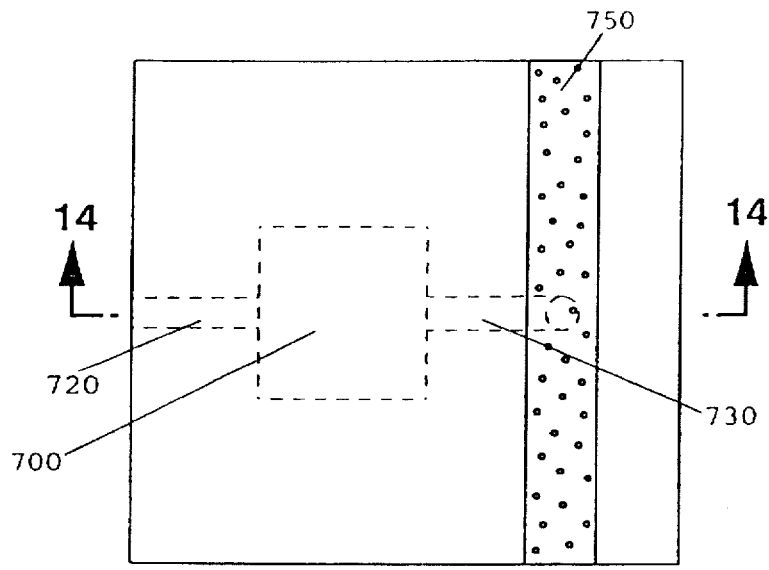
FIG. 13 is a top plan view of a sixth embodiment of the device of the present invention.
Figure 14:
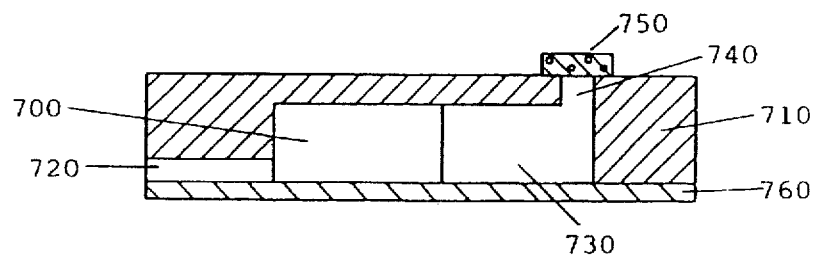
FIG. 14 is a cross-sectional view of the embodiment shown in FIG. 13 along lines 14—14.
Figure 15:
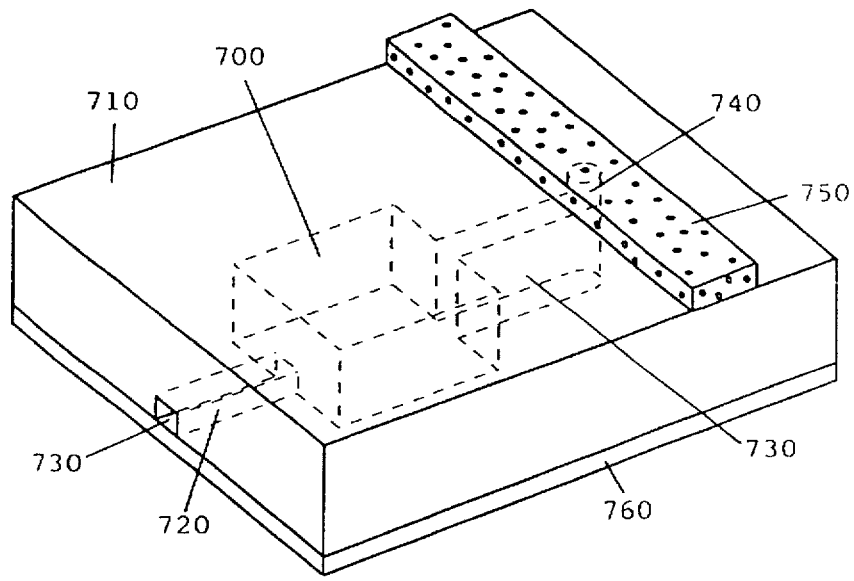
FIG. 15 is a perspective view of the embodiment shown in FIGS. 13 and 14.

FIGS. 13–15 show such another embodiment of the device of the present invention. FIG. 13 is a top plan view of an embodiment showing a well (700) which could be part of larger testing region (not shown) on a housing (710) of the device of the present invention. A channel (720) is indicated for liquid communication with a liquid receiving port (not shown). On one side of the well (700) there is a vent channel (730) terminating at a conduit (740). The conduit (740) extends toward the surface of the housing (710) to a gas-venting, liquid barrier (750). The well (700) is enclosed on one side by a base (760).

FIG. 14 shows the barrier (750) in cross-sectional view of FIG. 13 along lines 14—14 and FIG. 15 shows the embodiment in a perspective view. Importantly, the barrier (750) does not cover the well (700). This placement of the barrier (750) has an impact on the nature of the background (i.e., opaque or transparent) for reading the reaction in the well (700). Since the housing (710) and base (760) can be made of transparent material, the background of the test will be transparent and can be read by transmitted light.

Referring now to specific components of the device, as used herein "hydrophobic" means surfaces on which water and aqueous fluids will not spontaneously spread but will form separated drops having a nonzero contact angle. In short, they are "nonwettable." By contrast, "hydrophilic" is a characterized by the fact that water will spread on a surface. In the case of a gas-venting hydrophobic membrane the pores can result from a variety of means of construction such as a fibrous construction with pores formed by spaces between fibers, or a tortuous path construction where the pores are crooked paths through the body of an otherwise solid material, as with an open pored sponge. To serve as a material which will vent gas but block the passage of aqueous liquid such a hydrophobic gas-venting membrane must be generally hydrophobic internally within its pore structure. Such hydrophobic property may be the result of using a membrane material which is inherently hydrophobic or by treating or coating a non-hydrophobic material to make its internal pore surfaces hydrophobic. The gas-venting material may also be incorporated into the device as a bulk structure instead of the membrane structure herein described in preferred embodiment.

By "gas-venting" it is meant that air, or other gas, can readily flow through the material. This is to be contrasted with mere molecular diffusion of gas, for example air or nitrogen or oxygen. By "fluidic communication" it is meant a fluid, ie., a liquid or gas, can readily flow from one element of the device to another.

In one embodiment, the hydrophobic, gas-venting barrier is designed from material obtained from Gelman Sciences Membrane and Device Division (Ann Arbor, Mich.). In particular, the barrier may be made of Repel™ and Versapel™, new microporous venting membranes. These membranes do not "wet-out" or "block-off" when used with liquids containing lipids and maintain a high air flow rate. The Repel™ and Versapel™ hydrophobic membranes allow the passage of gases but prevent the entry of liquid.

In another embodiment, the hydrophobic, gas-venting barrier is made of expanded, sintered polytetrafluoroethylene (PTFE) in the manner described in U.S. Pat. Nos. 3,953,566 and 4,187,390 to Robert W. Gore, hereby incorporated by reference. The expanded, sintered "Teflon" exhibits a much better gas flow rate than the unexpanded, unsintered starting material.

In addition to those already mentioned, many other hydrophobic materials may be used to construct porous structures, including: polypropylene, polycarbonate, polyvanilidine chloride (PVDC), and polyvanilidine difluoride (PVDF). Furthermore, non-hydrophobic materials, such as polysulfone, may be used if they are treated to render the surfaces within the pores hydrophobic. Porous hydrophobic materials are generally available in the form of filters and are manufactured by various filter manufacturers such as Gelman Scientific, and Cuno Filtration. While these materials pass gas readily they will block the flow of aqueous liquids until a much higher pressure is reached. It is not unusual for such materials to require 30 to 40 psi of liquid pressure in order to permit any liquid to pass, and in the case of some materials, the pressures necessary to force liquid through them can be several hundreds of psi.

In another embodiment, the barrier is designed from material obtained from Porex Technologies Corp. of Georgia which has developed an innovative polymer composite known as LABPOR™ Microseal Material. When exposed to aqueous fluids, this material has the unique property of forming a permanent occlusive seal within the pore structure of the molded part. In other words, the material when contacted by aqueous liquid, will seal itself against the passage of such liquid. When applied to the present invention, this combines the feature of venting a gas, while preventing the flow of a liquid out of the device. This sealing action will also take place with physiological fluids such as normal saline, urine, serum, and blood.

The membrane may be attached to the device during manufacture by any number of conventional technologies including: adhesive attachment, heat sealing, solvent sealing, chemical bonding and ultrasonic welding.

Ultrasonic welding is a preferred method of attaching the gas-venting membrane. For example, the membrane can be attached in the manner described in U.S. Pat. Nos. 4,948,442 and 5,047,215 to Roy Manns, hereby incorporated by reference.

The non-venting membrane or "tape" which can be affixed to the outer side of the gas-venting membrane can be any of a number of polymer materials all of which are relatively impermeable to water vapor, but each of which has a different oxygen diffusion rate. Since the absolute oxygen diffusion rate is dependent on both the type and the thickness of the polymer, the particular type and thickness of polymer material used is selected to provide the desired oxygen level within the device.

Although embodiments have been described with some particularity, many modifications and variations of the preferred embodiment are possible without deviating from the invention.

EXPERIMENTAL

The following examples serve to illustrate certain preferred embodiments and aspects of the present invention and are not to be construed as limiting the scope thereof.

In the experimental disclosure which follows, the following abbreviations apply: μl (microliters); °C. (Centigrade); psi (pounds per square inch).

EXAMPLE 1

In this example, the design of a prototype device is described. A 24-well prototype device or "MicroCard" with approximate dimensions of 2"×2"×⅜" was constructed. This size is generally compatible with a standard Kodak™-style automated "Carousel" slide projector slide tray. The prototype device was made of an acrylic body with an acrylic sheet affixed to one side and a gas-venting barrier affixed to the other. The gas-venting, liquid barrier was made of PTFE. The body contained an inlet port and channels by which fluid introduced into the inlet port under positive pressure could be channelled to each of the 24 wells also formed in the body. All of the wells were each filled with a basal medium and a redox color indicator. In addition, each well contained a different substrate. The basal medium, color indicator, and substrates were dried within the device. The venting capabilities of the device were shown by injecting an aqueous bacterial suspension by pipette into the inlet port. The suspension flowed smoothly and easily into the device, filling all the wells. As the suspension entered the device, the air escaped easily through the gas-venting material, yet when the device was full and all the gas had exited, none of the fluid escaped through the gas-venting material. Upon incubation, color was formed in the wells and was visible through the non-venting, clear acrylic sheet.

EXAMPLE 2

A testing device manufactured by Vitek™ Systems in conformance with U.S. Pat. No. 4,038,151 (Fadler et al.) which is normally filled using a vacuum chamber, was modified by removing the oxygen-diffusing permeable but non-porous, non-venting film from one of its sides and replacing it with a PTFE membrane (pore size of approximately 0.1 micron) to serve as a gas-venting, liquid barrier. This membrane was affixed to the Vitek™ card by use of an adhesive. This modified device was easily filled with liquid introduced into its filling port under positive pressure from a transfer pipette. No vacuum chamber was required. In a separate experiment the bacteria identification chemistry which is the subject of U.S. Pat. No. 4,129,483 (Bochner) was shown to perform correctly in the Vitek™ card filled in the usual manner. It has also been shown that the color formed in the Vitek™ card by the Bochner chemistry is easily read by the Vitek™ reader.

EXAMPLE 3

In this example, a gas-venting material is formulated from non-venting starting material. An extruded, calendared, unsintered "Teflon" 6A poly(tetrafluoroethylene) film is made using the procedure described in U.S. Pat. Nos. 3,953,566 and 4,187,390 to Robert W. Gore. This film can be expanded and amorphously locked. Expansion is carried out at a temperature of about 300° C., and amorphous locking at about 370° C.

When an effort is made to flow water through the (air saturated) expanded, amorphous-locked film described above using 5 psi water pressure, no flow will occur. However, when the applied water pressure exceeds 10 psi, flow will start. Flow of air through the expanded sintered membrane is quite good at both 5 and 10 psi. However, the unexpanded, unsintered film will have extremely low gas flow rates.

From the above, it should be clear that the invention represents a much improved and fundamentally different design permitting air to escape during filling by use of a gas-venting, liquid barrier. In this manner, flow discrimination is made between liquids and gasses without the need for a valve-like mechanism, or any moving parts.

I claim:

1. A device comprising: a) a housing; b) a testing region having a plurality of test wells contained within said housing; c) a liquid receiving means at an external surface of said housing; d) a liquid flow-directing means comprising channels providing liquid communication between said plurality of test wells and said liquid receiving means; and e) a single gas-venting, liquid barrier comprising a hydrophobic membrane in fluidic communication with said testing region in contact with said test wells, wherein said hydrophobic membrane contains pores that permit passage of gas at positive pressure greater than 1 pound per square inch, but which blocks the passage of liquid at pressures less than 75 pounds per square inch.

2. The device of claim 1, wherein said barrier material is selected from the group comprising polycarbonate, polypropylene, polyvanilidine chloride, polyvanilidine difluoride, and polysulfone.

3. The device of claim 1, wherein said barrier comprises hydrophobic material.

4. The device of claim 3, wherein said material comprises expanded, sintered polytetrafluoroethylene.

5. The device of claim 1, wherein said testing region comprises one or more test wells.

6. The device of claim 5, wherein said liquid flow-directing means comprises channels internal to said housing to each of said one or more test wells in said testing region.

7. The device of claim 6, wherein said barrier is adapted to enclose at least a part of one of the sides of said one or more wells.

8. The device of claim 7, wherein said barrier is a membrane.

9. The device of claim 7, wherein said barrier is internal to said one or more wells.

10. The device of claim 9, wherein a conduit provides fluidic communication between said well and said barrier.

11. A testing device comprising:
a) a housing having a testing region;
b) a plurality of test wells containing a test formula comprising basal medium, one or more carbon sources, and a redox indicator disposed within said testing region;
c) a liquid receiving means at an external surface of said housing;
d) a liquid flow-directing means comprising channels internal to said housing providing liquid communication between said test wells and said liquid receiving means; and
e) a single gas-venting, liquid barrier comprising expanded, sintered polytetrafloroethylene in fluidic communication with said test wells, allowing for passage of gas at positive pressures greater than 1 pound per square inch, but blocking the passage of liquid at pressures less than 75 pounds per square inch.

12. The device of claim 11, wherein said barrier comprises hydrophobic material.

13. The device of claim 11, wherein said liquid receiving means comprises a liquid entry port.

14. The device of claim 13, wherein said liquid entry port has internal grooves.

15. A testing device comprising:
a) a housing containing a plurality of test wells, each well containing at least one test chemical;
b) a liquid receiving means on an external surface of said housing;
c) a liquid delivering means providing liquid communication between said wells and said liquid receiving means; and
d) a gas-venting, liquid barrier comprising expanded, sintered polytetrafloroethylene in fluidic communication with said test wells, allowing for passage of gas at positive pressures greater than 1 pound per square inch, but blocking the passage of liquid at pressures less than 75 pounds per square inch.

16. The device of claim 15, wherein said barrier is made of hydrophobic material.

17. The device of claim 15, wherein said gas-venting liquid barrier is made of material which, when contacted by aqueous liquid, will seal itself against the passage of said aqueous liquid.

18. The device of claim 17, wherein said barrier is a membrane.

19. The device of claim 17, wherein said membrane is adapted to enclose at least a part of one side of said wells.

20. The device of claim 19, further comprising a non-venting material, wherein said non-venting material is attached to said outer surface of said gas-venting barrier such that said device is sealed.

21. The device of claim 20, wherein said non-venting material comprises plastic film.

* * * * *